United States Patent [19]

Butler

[11] Patent Number: 5,268,549
[45] Date of Patent: Dec. 7, 1993

[54] METHOD AND APPARATUS FOR DESTROYING A SYRINGE NEEDLE

[76] Inventor: William F. Butler, 680 Atlanta Country Club Dr., Marietta, Ga. 30067

[21] Appl. No.: 889,041

[22] Filed: May 26, 1992

Related U.S. Application Data

[63] Continuation-in-part of Ser. No. 532,021, Jun. 1, 1990, Pat. No. 5,091,621, which is a continuation-in-part of Ser. No. 840,102, Feb. 24, 1992.

[51] Int. Cl.$^5$ .............................................. B23K 11/22
[52] U.S. Cl. ......................................................... 219/68
[58] Field of Search .............................. 219/68; 83/944

[56] References Cited

U.S. PATENT DOCUMENTS

| | | | |
|---|---|---|---|
| 3,770,930 | 11/1973 | Tang | 200/61.64 |
| 4,275,268 | 6/1981 | Greenhouse | 83/167 |
| 4,315,448 | 2/1982 | Ball | 83/167 |
| 4,404,881 | 9/1983 | Hanifl | 83/167 |
| 4,534,437 | 7/1985 | Szablack et al. | 83/165 |
| 4,628,169 | 12/1986 | Ch'ing-Lung | 219/68 |
| 4,877,934 | 10/1989 | Spinello | 219/68 |
| 4,890,006 | 12/1989 | Huang | 200/11 C |
| 4,961,541 | 10/1990 | Hashimoto | 219/68 |
| 4,965,426 | 10/1990 | Colombo | 219/68 |
| 5,076,178 | 12/1991 | Kohl et al. | 219/68 |
| 5,091,621 | 2/1992 | Butler | 219/68 |
| 5,138,124 | 8/1992 | Kirk et al. | 219/68 |
| 5,212,362 | 5/1993 | Burden et al. | 219/68 |

*Primary Examiner*—Geoffrey S. Evans
*Attorney, Agent, or Firm*—Jones & Askew

[57] ABSTRACT

A method and apparatus for sterilizing and destroying a syringe needle, having a housing, first and second walls in opposed relationship in the housing and defining therebetween a needle burn chamber, the distance between the first and second surfaces being at least the length of the needle, the first surface defining an opening therethrough, a needle receiver in the chamber, a first electrical contact on the needle receiver, a second electrical contact comprising an electrically conductive surface secured within the burn chamber and or added substantially perpendicular to the face of the needle receiver and the surface in alignment with the central line of the needle receiver, power source connected to the first and second contacts and, a waste collector disposed in the housing beneath and in communication with the burn chamber, the waste collector being removable from the housing; so that when the needle is inserted through the opening, it is in contacting relationship with the first electrical contact, the length of the needle then engages the second electrical contact closing the circuit between the contacts and melting the needle along at least most of its length with the resultant melted waste falling into the waste collector.

16 Claims, 5 Drawing Sheets

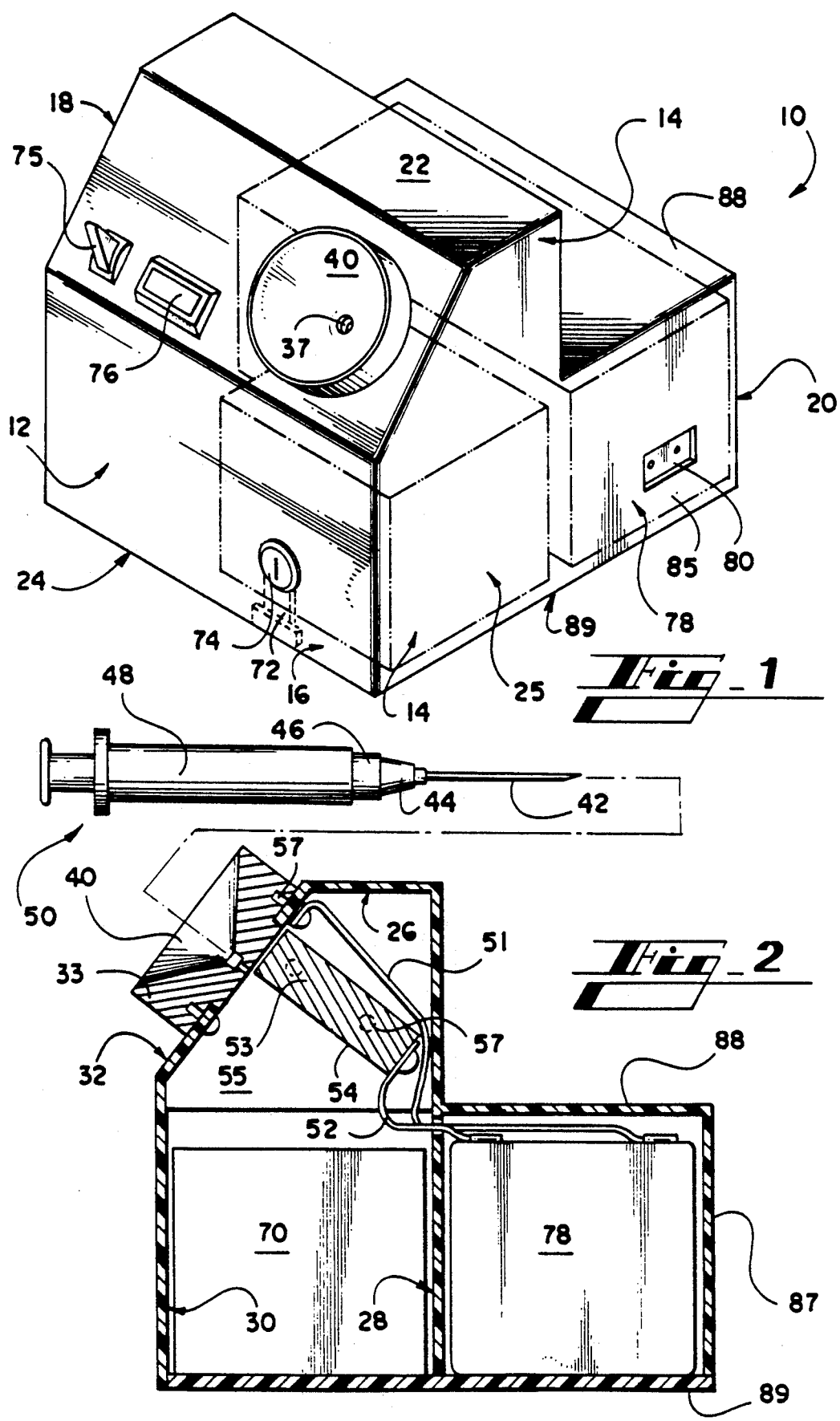

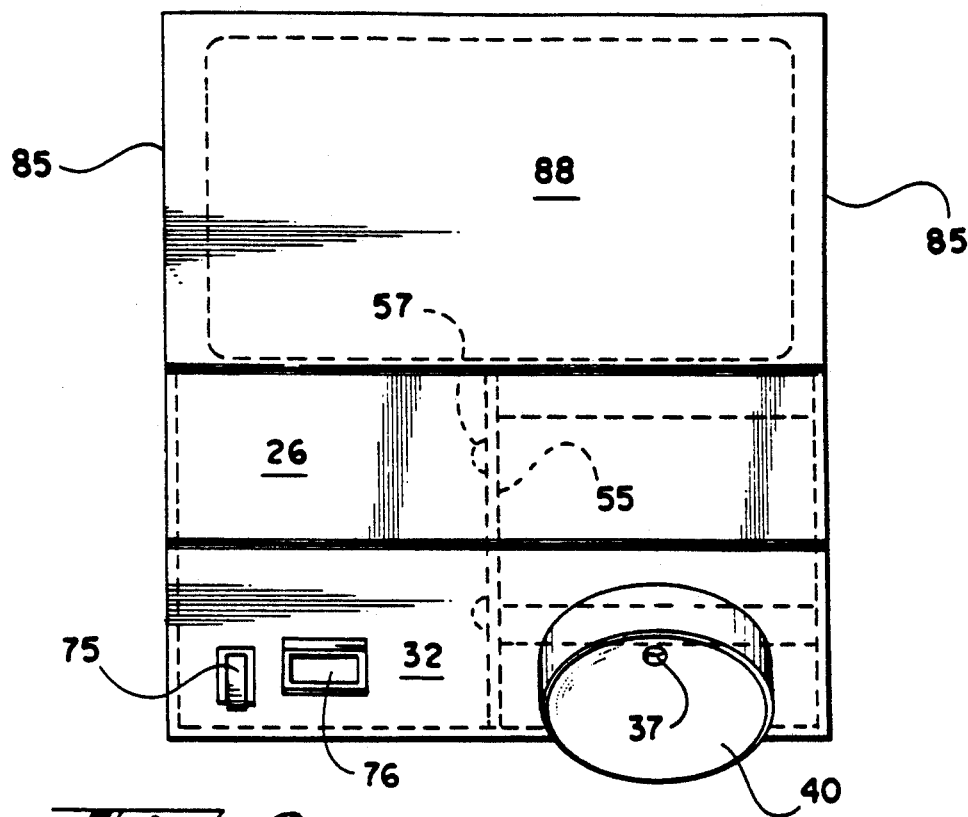
Fig_3
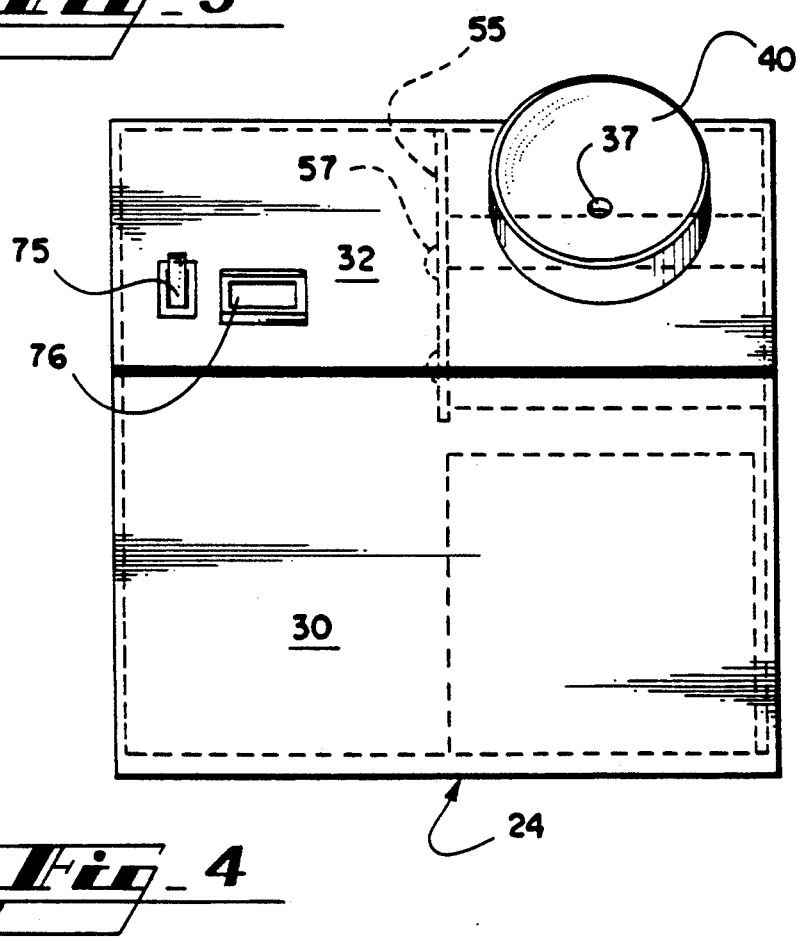
Fig_4

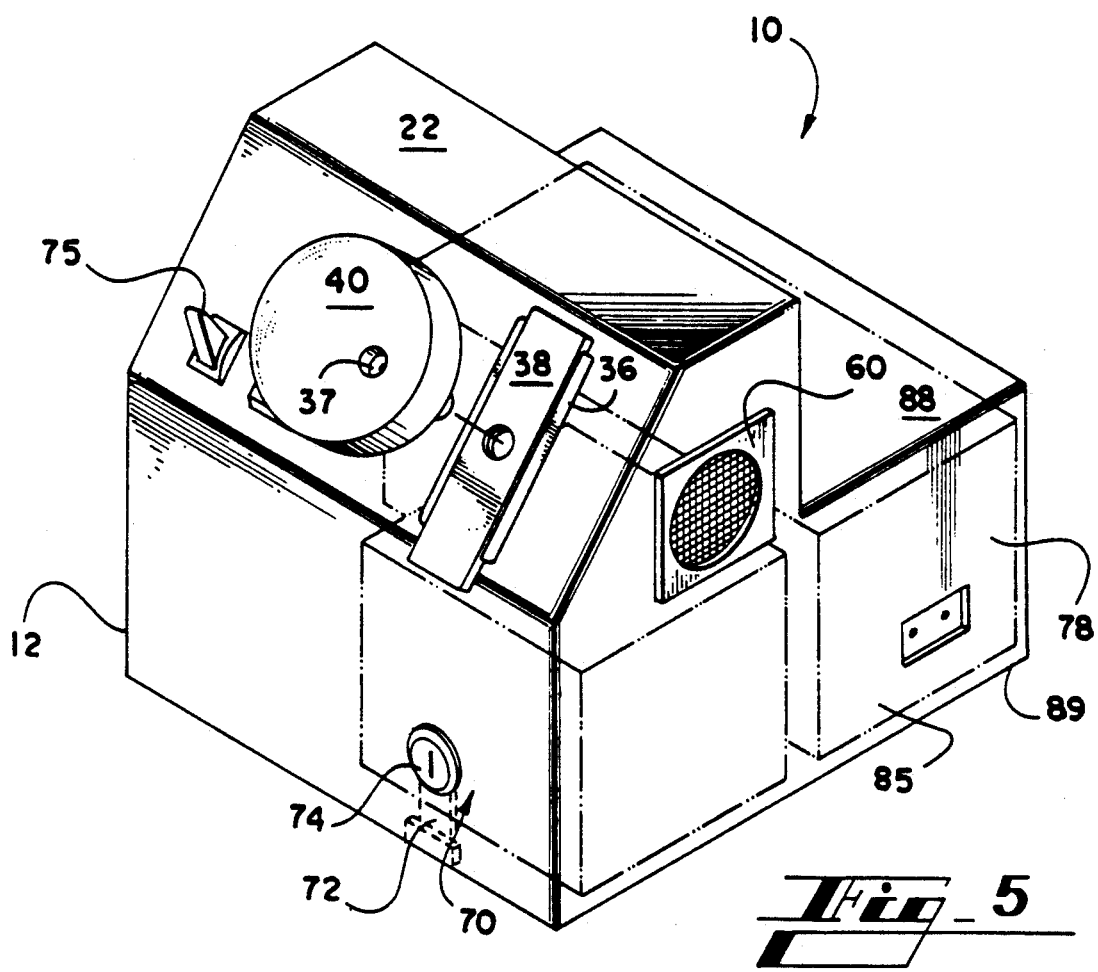
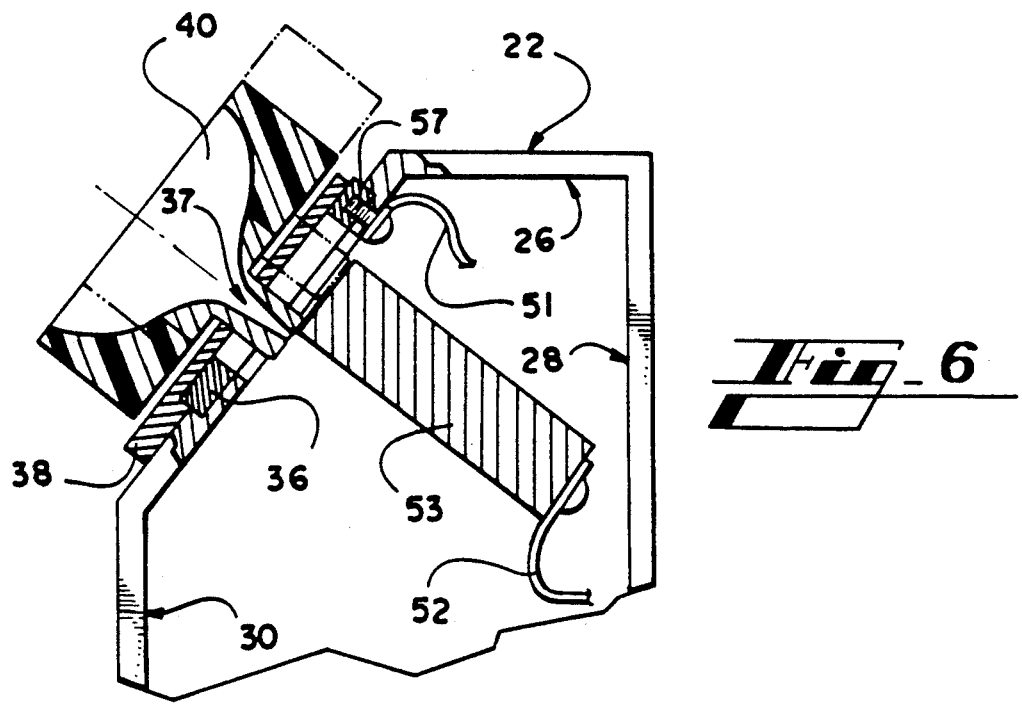

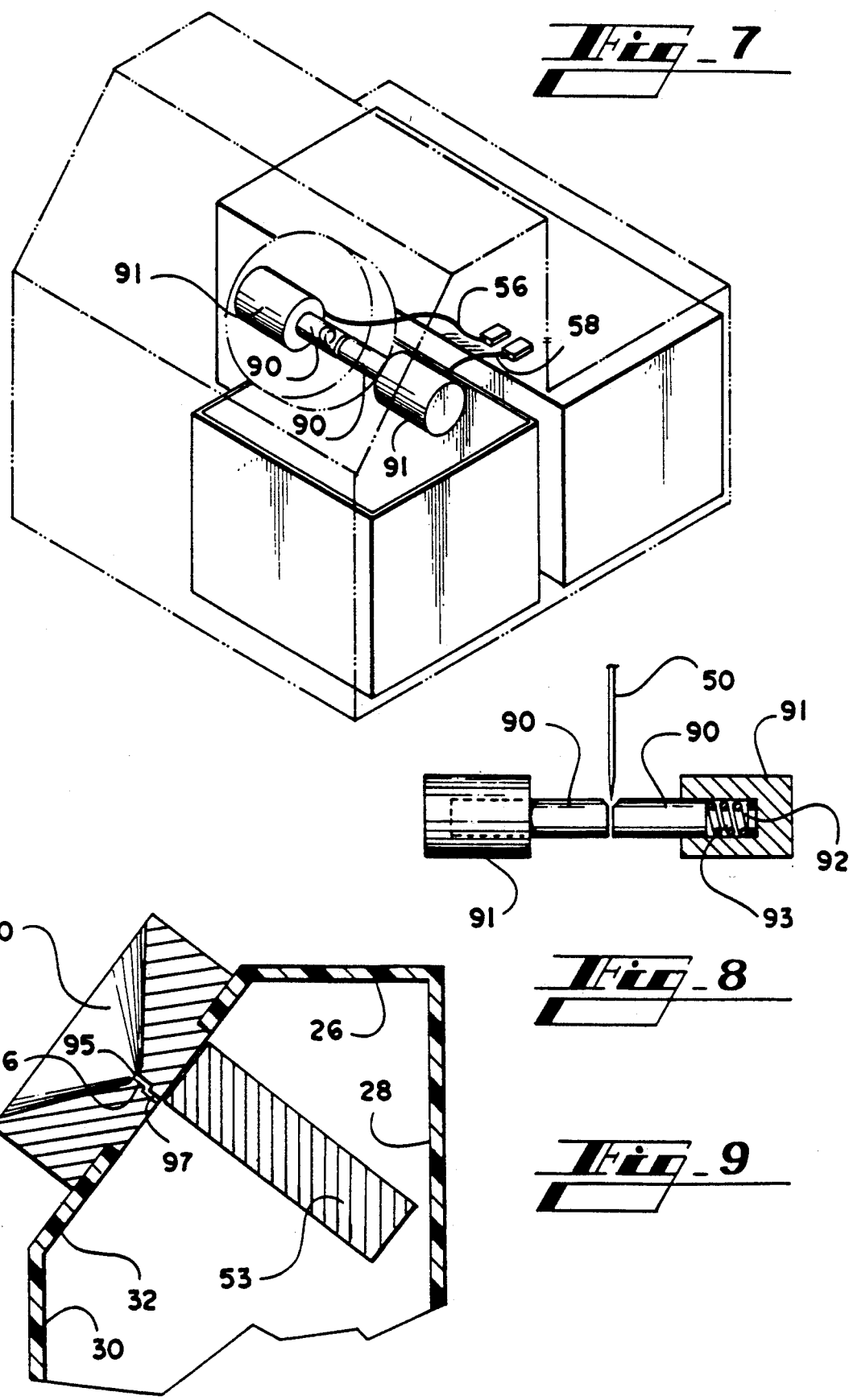

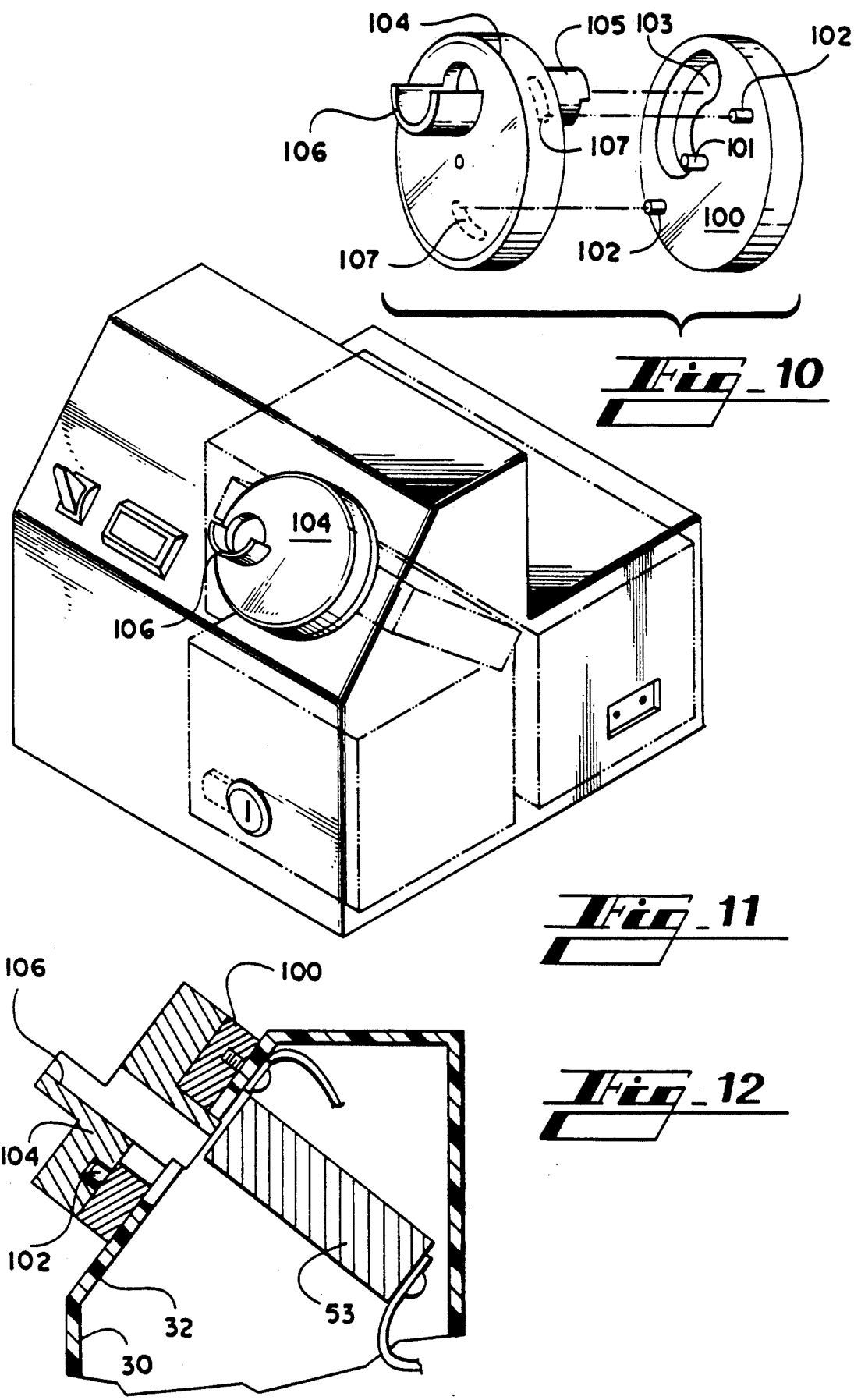

METHOD AND APPARATUS FOR DESTROYING A SYRINGE NEEDLE

CROSS-REFERENCE TO RELATED APPLICATION

This is a continuation-in-part of pending U.S. patent application Ser. No. 07/532,021, filed Jun. 1, 1990 now U.S. Pat. No. 5,091,621. This is also a continuation-in-part of U.S. patent application Ser. No. 07/840,102 filed Feb. 24, 1992.

TECHNICAL FIELD

This invention relates to a method and apparatus for destroying the needle portion of a syringe. In particular, the present invention relates to a method and apparatus that heats, sterilizes and removes the needle portion of a syringe after the needle has been used on a patient.

BACKGROUND OF THE INVENTION

The threat of infectious diseases, in particular AIDS and hepatitis B, is very prevalent today in hospitals and doctors' offices as a result of the use of hypodermic syringes. The Centers for Disease Control in Atlanta has extensively studied accidental syringe sticking incidents and have logged where most of the accidents occur and to whom. The Centers' records indicate that nurses experience more incidents than most other medical personnel.

Recovering the needle with the plastic tip cover provided with the syringe after use has not solved the problem because the cover can slip off or a person can be stuck by merely attempting to place the cover on the needle. Other means presently utilized for the disposal of used syringes still leave the steel of the hypodermic needle on the syringe, thereby exposing the waste handlers to the possibility of being pricked. The present syringe disposal systems are also very expensive.

The prior art includes the apparatus disclosed in U.S. Pat. No. 4,628,169 which describes an apparatus for melting only the tip of the needle, with the remainder of the metal on the syringe being detached by a separate operation. The remaining metal portion may still be contaminated. That system still leaves the possibility of the person collecting the remaining needle portion being exposed to microorganisms. Also, any infectious fluids are still available to flow out of the now-open plastic portion of the syringe.

U.S. Pat. No. 4,877,934 discloses a needle destroying apparatus which utilizes converging electrodes. The hypodermic syringe is inserted into the apparatus in a vertical orientation and is either slid onto a bottom electrode ramp or an electrode that can slide toward the bottom electrode thereby destroying the needle. However, because of the vertical orientation of the needle as it is inserted into the apparatus, the burnt needle tends to bend away from the ramp and loses contact with the bottom electrode. In addition, because of the vertical orientation, the burnt needle tends to collect on the bottom electrode thereby fouling the surface of the bottom electrode.

What is needed is a needle destruction apparatus that is easy to operate and will reliably destroy the needle efficiently. What is further needed is an apparatus that can be used in the clinic that can be used for long periods of time before it has to be taken apart and cleaned. An apparatus is needed that will treat used syringes to prevent storage of live viruses and other microorganisms in unsealed containers at room temperature, causing unwanted aerosol vapor to contaminate room air breathed by health care workers and patients.

SUMMARY OF THE INVENTION

The present invention is an apparatus for destroying a syringe needle comprising a housing and first and second non-horizontally oriented walls in opposed relationship in the housing and defining therebetween a needle burn chamber. The distance between the first and second surfaces is at least the length of the needle and the first surface defining an opening therethrough. The apparatus further comprises a preferably non-vertically oriented needle receiving means, a first electrical contact on the needle receiving means and an electrically conductive surface which is secured within the needle burn chamber. The electrically conductive surface serves as the second electrical contact. A power means is connected to the first and second electrical contacts. The needle is inserted in a non-vertical manner through the opening to be in contacting relationship with the first electrical contact, the needle receiving means. The length of the needle engages the electrically conductive surface or second contact, closing the circuit between the contacts and melting the needle along at least most of its length.

The device further comprises a housing having a battery power source, such as a 12-volt battery, and associated circuitry. A needle burning chamber is provided in the housing that has a stationary first electrical contact that is mounted on one wall of the chamber. The second contact is mounted within the chamber. Optionally, a waste receiving means is located beneath the burning chamber. The battery can be readily or continuously re-charged. In addition, the apparatus can be operated from conventional 110 volt or 220 volt power sources.

In operation, the power source is energized and the metal needle portion is inserted in a preferably non-vertical manner through the opening and into the needle receiving means. Most of the needle is inserted until the length of the needle is enclosed within the burn chamber. While the butt of the needle remains in contact with the first electrical contact, most of the needle length contacts the second electrical contact. The needle completes the circuit and acts as a jumper between the two electrical contacts. The current then melts the entire length of the needle. The melted metal drops into an optional waste receiving means to be collected at a later time.

The plastic portion of the needle is then withdrawn from the needle receiving means. It can be retrieved for recycling or can be disposed of by conventional waste handling methods.

An additional aspect of the present invention includes a means for sealing off any metal remaining on the syringe. This aspect includes a first electrical contact in the form of a sliding plate. The sliding plate has a first opening through which a needle may be inserted. A second fixed plate is secured to the housing and receives the sliding plate. The fixed plate has a second opening that is aligned to the first opening on the sliding plate when the sliding plate is at rest. If there is any metal remaining on the syringe after the needle has been subjected to the first and second electrical contacts, the user pushes the body of the syringe, still inserted in the burn chamber, upward. The sliding plate slides upwardly relative to the fixed plate. The metal remaining on the syringe seals as it contacts the outer surface of the fixed plate.

It is, therefore, an object of the present invention to provide a safe, low cost, efficient and easy to use device for sterilizing and destroying the metal needle of a hypodermic syringe, thereby killing any infectious microorganism that may be present in or on the needle.

Another object of the present invention is to completely remove the metal needle from a syringe while simultaneously sealing the plastic portion of the syringe.

Another object of the present invention is to provide an apparatus that can be used for long periods of time between cleaning of electrodes.

Another object of the present invention is to provide an apparatus that will reliably sterilize hypodermic needles.

Another object of the present invention is to prevent unwanted contact with a needle contaminated with an infectious organism by physically destroying at least most of the length of the needle and sterilizing the remainder thereof thereby eliminating the spread of infectious diseases through contaminated hypodermic needles.

Yet another object of the present invention is to provide an apparatus that can reliably and safely sterilize and destroy the needle portion of a hypodermic syringe and can be used safely in a clinic or in a physician's office.

Another object of the present invention is to provide an apparatus that can sterilize and destroy the needle portion of a hypodermic syringe so that the destroyed residue of the needle portion can be safely and inexpensively disposed of by conventional means.

A further object of the present invention is to provide a safe and effective means for sealing any metal that may remain on the syringe.

A further object of the present invention is to eliminate viruses in a needle destroying mechanism thereby preventing aerosol contamination of the personnel and patient environment.

These and other objects, features and advantages of the present invention will become apparent after a review of the following detailed description of the disclosed embodiments and the appended claims.

BRIEF DESCRIPTION OF THE DRAWINGS

FIG. 1 is a perspective view of the present invention.

FIG. 2 is a side view in partial cross-section of the device of FIG. 1.

FIG. 3 is a top view of the device of FIG. 1.

FIG. 4 is a front view of the device of FIG. 1.

FIG. 5 is a perspective view of a first alternative embodiment of FIG. 1.

FIG. 6 is a partial cross-section view of the device of FIG. 5.

FIG. 7 is a perspective view of a second alternative embodiment of the present invention.

FIG. 8 is an enlarged view of a portion of the device of FIG. 7.

FIG. 9 is a cross-sectional view of a third alternative embodiment of the present invention.

FIG. 10 is an enlarged exploded view of a portion of the device of FIG. 11.

FIG. 11 is a perspective view of a fourth alternative embodiment of the present invention.

FIG. 12 is a cross-sectional view of the device of FIG. 11.

DETAILED DESCRIPTION

The present invention is a method and apparatus for destroying the needle portion of a hypodermic syringe. The present invention is, in part, an apparatus that is capable of simultaneously sterilizing and destroying the needle portion of a hypodermic syringe and thereby eliminating the risk of infection by a microorganism that may be present in or on the needle.

When a syringe is inserted into the apparatus that comprises the present invention, the needle is heated to a temperature of at least 1750° C. This temperature is capable of inactivating any virus, bacteria, yeast or other microorganism. In addition to being heated, the needle is melted so that it is removed from the remaining portion of the syringe. The nub remaining after the needle is melted and sealed so that no fluid can leak from the syringe.

Referring now to FIGS. 1 through 4, the numeral 10 denotes generally the present invention which comprises a housing 12, a burning chamber 14 and waste collection means 16. The housing 12 can be made of any suitable material, such as metal, plastic or the like so long as the material is capable of maintaining structural integrity if exposed to sparks caused by the melting needle. The housing 12 is generally defined with side surfaces 18, end surfaces 20, a top surface 22, and a bottom surface 24. It is to be understood that the apparatus according to the present invention can be mounted to a wall or a surface such as the bottom of a wall cabinet or set on a counter.

The burning chamber 14 occupies the forward end of the housing 12 and preferably is constructed of a heat resistant material. The burning chamber 14 is defined by side chamber walls 25, a chamber top 26, rear chamber wall 28, front chamber wall 30 and a preferably non-vertical front face wall 32. A first electrical contact 33 is mounted on the front face wall 32. As seen more clearly in FIG. 2, the first electrical contact 33 is a conical shaped port 40 which is mounted to the front face wall 32 of the burning chamber 14 by means of screws 5. The first electrical contact 33 is connected by wire 51 to a battery 78. The port 40 tapers downwardly in the outer center surface and has an opening 37 disposed therethrough. The port 40 and opening 37 are dimensional to receive the metal needle portion 42, the neck portion 44, shoulder portion 46 and body portion 48 of a hypodermic needle 50.

A second electrical contact is a block 53 mounted within the burning chamber 14 to the rear chamber wall 28 and top 26 by means of mounting brackets 55 and screws 57. The block 53 is rectangular in shape with its lower surface 54 aligned perpendicular with the front face wall 32. The centerline of the lower surface 54 is coaxial with the centerline of the opening 37 of the port 40. Wire 52 connects the block 53 with the electrical circuitry within the housing 12 through rear chamber wall 28. The block 53 is preferably made of carbon.

The diameter of opening 37 can be of such size as to accept conventional 22-, 18-, 14- or any other gauge stainless steel needles therethrough. Additionally, the device 10 may incorporate a plurality of needle receiving means so that a single device 10 may be used to destroy a number of different style and diameter needles, such as, for example, intravenous, butterfly and catheter placement needles.

The optional waste collection means 16 is disposed beneath and in communication with the burn chamber 14 and comprises a tray 70 that is slidably removable from housing 12, as shown in FIG. 2. The tray 70 receives therein the melted needles that result from the operation of the device 10.

The tray 70 is retained within the housing 12 by means of a locking arm 72 that is operatively connected to the keylock 74. The keylock 74 is a safety feature, ensuring that only authorized personnel open the device 10. By turning a key (not shown), the user turns the key lock 74 and releases the locking arm 72 and allows the tray 70 to be removed.

A toggle switch 75 is mounted to the front face 32 of the housing 12. An LED light 76 is also positioned on the front face 32 and when switch 75 is moved to the "ON" position the light is illuminated. The power source is normally a 12-volt battery 78 that is rechargeable through charging opening 80 in side surface 18. The battery 78 is housed on the rear of the burning chamber 14 and is contained by rear chamber wall 28, battery side walls 85, battery rear wall 87, battery top wall 88, and battery bottom wall 89. A second LED light, not shown, may be provided to indicate that the charging circuit is in use. A conventional breaker can be used in place of the fuse.

An electric fan 60 shown in FIG. 5 is mounted to one of the side chamber walls 25, adjacent to the tray 70. Wire 51 connects the fan with the electrical circuitry within the housing 12 through the rear chamber wall 28. Thus, the fan is activated when the switch 75 is moved to the "ON" position.

OPERATION

To operate the device 10, the user flips the switch 74 to the "ON" position, which in turn allows electricity to flow from battery 78 to the first electrical contact 33 and to block 53. The light 76 will also be illuminated, indicating that the device 10 is operative. The fan 60 will also be energized.

The user inserts the needle 50 into the port 40 until the shoulder 46 engages the port. When the length of the needle 50 is enclosed within the burning chamber 14, the user causes the length of the needle to contact the block 53. Because the shoulder portion 46 is in contact with the first electrical contact 33, the needle portion 42 then acts as a jumper between contact 33 and block 53, closing the circuit and melting the needle portion 42. The majority of the metal needle portion 46 melts off of the needle 50 and falls into the tray 70.

Once the needle 50 is sealed, the user withdraws the needle 50 from the device 10. Another needle 50 may be inserted into the device 10 or the device 10 can be de-energized by turning the switch 75 to the "OFF" position. The light 76 will then go off, indicating that the device 10 is inoperative.

Waste material in tray 70 can be removed by turning the keylock 74 to the "UNLOCK TRAY" position. The contents of the tray 70 are sterile, so they can be disposed of as normal waste materials. The tray 70 will contain no contaminated metal so incidents of infection will be eliminated. The remaining body portion 48 of the needle 50 can be recycled as sterilized plastic.

FIRST ALTERNATIVE EMBODIMENT

As seen more clearly in FIGS. 5 and 6, the first alternative embodiment is similar to the device shown in FIGS. 1 through 4 except that the first electrical contact 33 is mounted on the front face wall 32 of the burning chamber 14 and comprises a fixed plate 36. A sliding plate 38 is in sliding relation within the fixed plate 36. A conical shaped port 40 is threadably mounted on the sliding plate 38. The port 40 tapers downwardly through the sliding plate 38 which exits the face of fixed plate 36. The fixed plate 36 has an opening 37 centrally disposed therethrough. The port 40 and opening 37 are dimensional to receive the metal needle portion 42, the neck portion 44, shoulder portion 46 and body portion 48 of a hypodermic needle 50. Wire 51 connects the fixed plate 36 with the electrical circuitry within housing 12 through rear chamber wall 28.

The second electrical contact 52 is a block 53 and is structured in the same manner described above for the device shown in FIGS. 1 through 4.

In operation, the first alternative embodiment operates initially similar to the embodiment described above. To operate the device 10, the user flips the switch 74 to the "ON" position, which in turn allows electricity to flow from battery 78 to the first electrical contact 33 and to block 53. The light 76 will also be illuminated, indicating that the device 10 is operative. The fan 60 will also be energized.

The user inserts the needle 50 into the port 40 until the shoulder 46 engages the port. When the length of the needle 50 is enclosed within the burning chamber 14, the user causes the length of the needle to contact the block 53. Because the shoulder portion 46 is in contact with the first electrical contact 33, the needle portion 42 then acts as a jumper between contact 33 and block 53, closing the circuit and melting the needle portion 42. The majority of the metal needle portion 46 melts off of the needle 50 and falls into the tray 70.

To seal off any remaining portion of the needle, the user moves the body of the syringe upwardly while shoulder 46 of the needle is flush against the port. This upwardly motion causes the sliding plate 38 to slide within the fixed plate 36. Any remaining metal on the needle 50 seals as it contacts solid surface of the fixed plate 36 above the opening 37 and seals the needle. While in operation, the optional fan 60 draws any unpleasant odors and smoke resulting from the molten metal out of the burn chamber and disperses the odors through a filter into the atmosphere.

SECOND ALTERNATIVE EMBODIMENT

A second alternative embodiment is shown in FIGS. 7 and 8. In lieu of the first electrical contact being an opening 37 on a sliding plate 38, it is contemplated that alternatively the first electrical contact comprise a pair of opposed, spring-loaded cylinders 90. Each of the cylinders 90 is mounted within a cylinder housing 91. The cylinder housing 91 has a chamber 92 that receives a spring 93 and the pin 90. The cylinder housings 91 are mounted in opposed relation to each other to the front face wall 32. Wires 56, 58 connect the cylinders 90 with the electric circuitry within the housing 12 through the rear chamber wall 28. The electric contact is made when pins contact the needle as it passes through the opening 37 and into the burning chamber 14.

THIRD ALTERNATIVE EMBODIMENT

A third alternative embodiment is shown in FIG. 9. The second alternative embodiment is similar to the preferred embodiment discussed above except for the opening 37. It is contemplated that the opening 37 may be dog-legged. The alternative embodiment in FIG. 8 has a port 40 and a stepped channel 95. The channel 95 has a first length 96 connected to a second parallel length 97. The lengths 96, 97 are not coaxial. When the needle 50 is inserted in the port 40, the needle must pass through both lengths of the channel thus better ensuring electrical contact at that point. It must be noted that the degree of offset between the first 96 and second 97 lengths of the channel 95 cannot be greater than the channel diameter. This is to enable the needle 50 to pass through the channel 95 in a direction substantially perpendicular with the front face wall 32 and to enable the length of the needle to contact the second electrical contact 52.

FOURTH ALTERNATIVE EMBODIMENT

A fourth alternative embodiment is shown in FIGS. 11-13. This alternative embodiment is directed to the bending of the remaining needle after that majority of its length has melted. The fourth alternative embodiment is similar to the preferred embodiment in that it has a housing 12, second electrical contact 52, burning chamber 14, and battery 78.

The fourth alternative embodiment however has a different mechanism for receiving the needle and for finishing the needle butt at the end of the melting process. The fourth alternative embodiment includes an inner disc 100 threadably mounted to the front face wall 32 of the burning chamber 14. An axle 101 extends outwardly from the center of the face of the inner disc 100. Two pins 102 extend outwardly from opposite halves of the face of the inner disc 100. A kidney shaped hole 103 is cut from the inner disc 100. An outer disc 104 is rotatably mounted on the inner disc 100 by means of the axle 101. An inner sleeve 105 is fixedly mounted to the inner surface of the outer disc 104. The kidney shaped piece 103 receives the inner sleeve 105 and enables the inner sleeve to rotate over a limited distance. A cup 106 is mounted to the outer surface of the outer disc 104. The cup supports and receives the syringe shoulder while the needle is inserted into the burning chamber 14. A pair of small, kidney shaped openings 107 are located on opposite halves of the inner face of the outer disc 104. The openings 107 receive the pins 102 mounted to the inner disc. The pins 102 provide support and enable the outer disc to rotate over a limited distance relative to the inner disc 100. The distance of rotation for the outer disc 104 is defined by the arc in the openings 107 and the kidney shaped piece 103.

In operation, the needle 50 is inserted and melted as discussed above for the preferred embodiment. After most of the length of needle has melted, any remaining needle is sealed by rotating the outer disc 104. This causes the needle 50 to bend as it contacts the outer surface of the inner disc 100.

It is to be understood that an important part of the present invention is preferred that the needle be inserted in a non-vertical orientation. The angle from the vertical can be between 10° and 90° with the more preferred angle range of between 20° and 75° with the most preferred angle range of approximately 45°.

It will be appreciated that the embodiments discussed above are the preferred embodiments, falling within the scope of the appended claims, and that various other alternative embodiments are contemplated. For example, the angle of the front face wall 32 may be altered to accommodate the user. Moreover, it is contemplated that the battery 78 may be stored below the burning chamber 14 for wall-mounted units.

What is claimed is:

1. An apparatus for destroying a syringe needle comprising:
    a. a housing;
    b. first and second walls in opposed relationship in the housing and defining therebetween a needle burn chamber, the first wall defining an opening therethrough;
    c. a needle receiving means having a central axis;
    d. a first electrical contact fixed to the needle receiving means;
    e. a second electrical contact comprising an electrically conductive surface secured within the needle burn chamber and oriented substantially parallel to the central axis of the needle receiving means wherein the second electrical contact comprising the electrically conductive surface contacts substantially the length of the needle after the needle is inserted into the needle receiving means; and
    f. power means connected to the first and second electrical contacts.

2. The apparatus of claim 1, further comprising a waste collecting means disposed in the housing beneath and in communication with the burn chamber.

3. The apparatus of claim 1 wherein the needle receiving means comprises a mounting plate having an opening therethrough and, an oblong plate having a second opening therethrough, the oblong plate being slidably received onto the mounting plate and the first and second openings being in alignment when the apparatus is in a static position.

4. The apparatus of claim 1 wherein the second electrical contact comprises a carbon block.

5. The apparatus of claim 1, wherein the surface is oriented at between approximately 10 degrees and 90 degrees from the vertical.

6. The apparatus of claim 1, wherein the surface is oriented at between approximately 20 degrees and 75 degrees from the vertical.

7. The apparatus of claim 1, wherein the needle receiving means is oriented approximately 45° from the vertical.

8. The apparatus of claim 1 wherein the first electrical contact comprises a pair of cylindrical housings in opposed relation, within the housings are mounted a pair of spring-loaded pins in opposed, abutting relation, the pins abutting at the opening.

9. The apparatus of claim 1, wherein the needle receiving means has an exterior surface and an interior surface, and the second opening through the needle receiving means is defined by a first axial length extending from the exterior surface, and a second axial length in communication with the first axial length and extending from the interior surface, the first and second axial lengths being non-coaxial, and the widths of the first and second lengths being greater than the degree of offset between the axis of the first and the axis of the second length.

10. The apparatus of claim 9, wherein the first and second axial lengths are parallel.

11. A method of destroying a syringe needle, having a metal portion, comprising the steps of:
    a) inserting the metal portion of a needle through a needle receiving means into a needle burn chamber, the needle receiving means having a first electrical contact fixed thereto and a second electrical contact fixed to the needle burn chamber;
    b) energizing the contacts; and c) causing the needle to engage the first electrical contact and a substantial portion of the length of the needle to engage the second electrical contact thereby closing the circuit between the contacts.

12. The method of claim 11, wherein the needle receiving means is between approximately 10° and 90° from the vertical.

13. The method of claim 11, wherein the needle receiving means is between approximately 20° and 75° from the vertical.

14. The method of claim 11, wherein the needle receiving means is approximately 45° from the vertical.

15. The method of claim 11, wherein the needle receiving means has an exterior surface and an interior surface, and the opening through the needle receiving means is defined by a first axial length extending from the exterior surface, and a second axial length in communication with the first axial length and extending from the interior surface, the first and second axial lengths being non-coaxial, and the widths of the first and second axial lengths being greater than the degree of offset between the axis of the first length and the axis of the second length.

16. The method of claim 11, wherein the first and second axial lengths are parallel.

* * * * *